(12) United States Patent
Zhang et al.

(10) Patent No.: US 10,638,771 B2
(45) Date of Patent: May 5, 2020

(54) **MUTANT STRAIN OF *LACTOCOCCUS LACTIS* AND ITS APPLICATION**

(71) Applicants: Juan Zhang, Wuxi (CN); Zhengming Zhu, Wuxi (CN); Jian Chen, Wuxi (CN); Guocheng Du, Wuxi (CN); Peishan Yang, Wuxi (CN)

(72) Inventors: Juan Zhang, Wuxi (CN); Zhengming Zhu, Wuxi (CN); Jian Chen, Wuxi (CN); Guocheng Du, Wuxi (CN); Peishan Yang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 224 days.

(21) Appl. No.: 15/640,903

(22) Filed: Jul. 3, 2017

(65) Prior Publication Data

US 2018/0042251 A1 Feb. 15, 2018

Related U.S. Application Data

(63) Continuation of application No. PCT/CN2016/108476, filed on Dec. 5, 2016.

(30) Foreign Application Priority Data

Aug. 10, 2016 (CN) .......................... 2016 1 0652096

(51) Int. Cl.
| | |
|---|---|
| *A23C 9/123* | (2006.01) |
| *A23L 19/20* | (2016.01) |
| *C12R 1/46* | (2006.01) |
| *A23B 7/10* | (2006.01) |
| *A23B 7/155* | (2006.01) |

(52) U.S. Cl.
CPC .............. *A23C 9/123* (2013.01); *A23B 7/105* (2013.01); *A23B 7/155* (2013.01); *A23L 19/20* (2016.08); *C12R 1/46* (2013.01); *A23V 2002/00* (2013.01); *A23Y 2240/41* (2013.01)

(58) Field of Classification Search
CPC ............ A23C 9/123; A23L 19/20; C12R 1/46
USPC ........................................................... 426/43
See application file for complete search history.

(56) References Cited

U.S. PATENT DOCUMENTS

2011/0200709 A1\* 8/2011 Folkenberg .......... A23C 9/1234
426/43

OTHER PUBLICATIONS

Rallu, F. Molecular Microbiology. 2000. 35: 517-528 (Year: 2000).\*
KR-2013096886—English Abstract (Year: 2013).\*

\* cited by examiner

*Primary Examiner* — Hamid R Badr
(74) *Attorney, Agent, or Firm* — Lili Chen

(57) ABSTRACT

The present invention relates to a mutant strain of *Lactococcus lactis* and its application, and belongs to the field of food biotechnology. The mutant strain, *Lactococcus lactis* WH101, was screened for its better tolerance to harsh environmental factors, especially higher acid tolerance. The $OD_{600}$ of *Lactococcus lactis* WH101 was increased by 5.5 times than that of the parent strain when cultured at pH 4.5. The survival rate of the mutant strain was 22.4 times higher than that of the parent strain after 3 hr treatment in pH 4.0 culture medium. The survival rate of the mutant strain was 5.2, 2.0 and 1.9 times over that of the parent strain treated with 15% ethanol for 4 hr, 15% NaCl for 6 hr and 1 mM $H_2O_2$ for 3 hr, respectively.

5 Claims, 1 Drawing Sheet

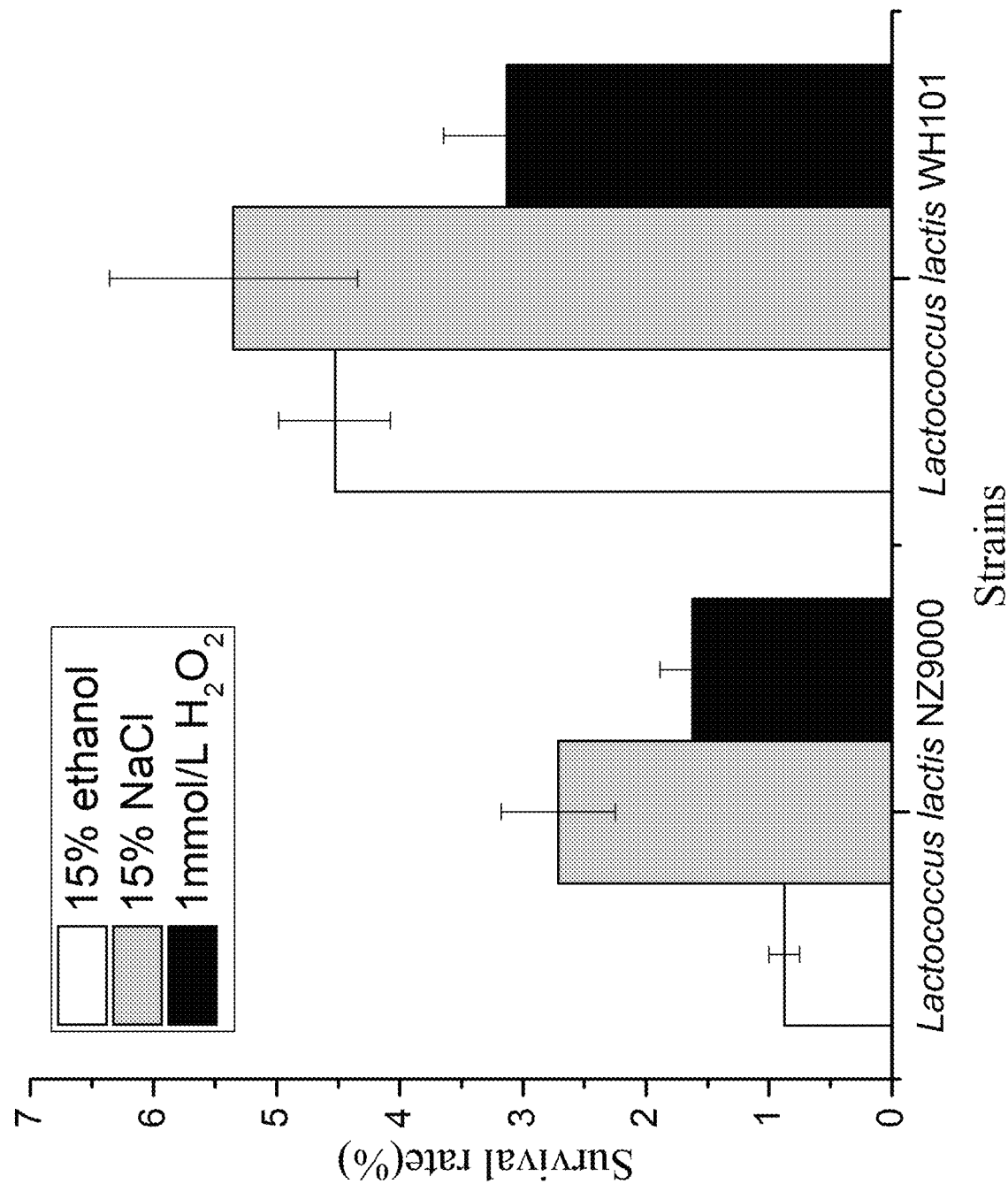

MUTANT STRAIN OF *LACTOCOCCUS LACTIS* AND ITS APPLICATION

CROSS-REFERENCES AND RELATED APPLICATIONS

This application claims the benefit of priority to Chinese Application No. 201610652096.9, entitled "A mutant strain of *Lactococcus lactis* and its application", filed Aug. 10, 2016 and is a continuation application of international application No. PCT/CN2016/108476, filed Dec. 5, 2016, which are herein incorporated by reference in their entirety.

BACKGROUND OF THE INVENTION

Field of the Invention

The present invention relates to a mutant strain of *Lactococcus lactis* and its application, and belongs to the field of food biotechnology.

Description of the Related Art

As an industrial microbial cell factory, *Lactococcus lactis* (*L. lactis*) has been widely used in food, fermentation and other fields. Acid production characteristic is an indispensable component of industrial microbial fermentation processes. On one hand, metabolic acids can help promoting cell energy conversion, maintaining the balance of intracellular osmotic pressure, and enhancing the environmental competitiveness of the microbial cells. On the other hand, with the accumulation of intracellular acid, it will result in microbial cellular pH unremitting decrease, and inhibition of the activity of enzymes necessary for maintenance of normal intracellular physiological function. Moreover, acid production of *L. lactis* has significant effects on the production cost, the downstream processing and the management of industrial emissions.

As a probiotic in human gastrointestinal tracts, *L. lactis* has to be tolerant to acid stresses, bile salt stresses and other gastrointestinal stresses in human intestinal environment. Therefore, improving the tolerance of *L. lactis* strains to acid stresses has become an urgent problem to be solved in the academic and industrial fields.

DETAILED DESCRIPTION

The goal of the present invention is to provide a mutant strain of *Lactococcus lactis* having increased acid tolerance compared to the parent strain. The mutant strain is *Lactococcus lactis* WH101 which was deposited on Apr. 29, 2016 in the Chinese Type Culture Collection with the accession CCTCC NO: M 2016233, Wuhan, Wuhan University. CCTCC is a international depositary authority under the Budapest Treaty that is an acceptable depositary under 37CFR 1.803. Applicants state that all restrictions on the availability to the public of the material so deposited will be irrevocably removed upon granting of a patent.

The *Lactococcus lactis* WH101 (CCTCC NO: M 2016233) was obtained by using diethyl sulfate as a mutagenic agent to mutagenize *Lactococcus lactis* NZ9000. The $OD_{600}$ of *L. lactis* WH101 cultures obtained under pH 4.5 reached 0.527 which was 4.5 times than that of the parent strain. The survival rate of *Lactococcus lactis* WH101 in lactic acid with pH 4.0 after 3 h was 22.4 times than that of the parent strain. Therefore, *Lactococcus lactis* WH101 (CCTCC NO: M 2016233) has better growth performance and acid tolerance compared to its parent strain.

The *Lactococcus lactis* WH101 can be used in producing fermentation food, such as kimchi and yoghurt. As it is known that the fermentative strains need to be subjected to high salt and low pH environment in fermentation process of kimchi. Because of the acid tolerance of *Lactococcus lactis* WH101 strain, the lactic acid bacteria can grow rapidly during initial fermentation and become the dominant species. Lactic acid and antibacterial substances produced by the lactic acid bacteria are nature preservatives and could inhibit the growth of other bacteria. For yogurt production, the use of acid tolerance strain *Lactococcus lactis* WH101 could enhance the fermentation performance of lactic acid bacteria under acidic environment, which could in turn improve the quality of the yogurt.

BRIEF DESCRIPTION OF DRAWINGS

FIG. 1. Survival rates of different *Lactococcus lactis* strains cultured under different environmental stresses. *Lactococcus lactis* WH101 and NZ9000 strains were cultured under 15% ethanol for 4 hr (white bar), 15% NaCl for 6 hr (gray bar) and 1 mM $H_2O_2$ for 3 hr (black bar), respectively.

EXAMPLES

Materials and Methods:
Medium: GM17 medium: glucose 5.0 g/L, tryptone 5.0 g/L, soybean peptone 5.0 g/L, beef extract 5.0 g/L, yeast extract 2.5 g/L, vitamin C 0.5 g/L, magnesium sulfate 0.25 g/L, glycerophosphate disodium 19.0 g/L. The pH of GM17 medium was adjusted with 25% lactic acid.

Example 1. Breeding of *Lactococcus lactis* (CCTCC NO: M 2016233)

*Lactococcus lactis* NZ9000 was used as the parent strain, which was cultured in GM17 medium until reaching the logarithmic growth phase. The concentration of bacterial solution was adjusted to $10^7$ CFU/ml, centrifuged at 5000 rpm for 10 min, washed and resuspended with 0.85% saline twice. An equal volume of GM17 medium containing 0.5% v/v diethyl sulfate (DES) was added to the *L. lactis* cells, and incubated at 30° C., 100 rpm for 30 min. The cells were immediately washed with 0.85% normal saline for 5 times, and resuspended in an equal volume of GM17 medium, and incubated at 30° C. for 1.5 hr.

1 ml GM17 (pH 5.0) medium was added to 96 deep well plates of 2.2 ml, and the *L. lactis* culture was inoculated into 96 deep well plates with the inoculation amount of 2%. The cells were incubated at 30° C. for 48 hours. The mutant strains were screened preliminarily according to the culture biomass, and then the mixed strains were diluted appropriately into pH 5.0 plates. The colonies were fermented at pH 5.0 and selected by the biomass. The $OD_{600}$ of parent strain cultured at pH 5.0 was 0.076, and the $OD_{600}$ of mutant strain *Lactococcus lactis* WH101 culture reached 0.612. The strain named *Lactococcus lactis* WH101 was deposited in the Chinese Type Culture Collection on Apr. 29, 2016 with the accession number CCTCC NO: M 2016233.

Example 2. Growth Performance of *Lactococcus lactis* (CCTCC NO: M 2016233) Under Acid Stresses

*Lactococcus lactis* NZ9000 and *Lactococcus lactis* WH101, which were preserved in −80° C. glycerol tube, were inoculated into GM17 medium at a 2% inoculation rate and incubated at 30° C. for 12 hours.

*Lactococcus lactis* NZ9000 and *Lactococcus lactis* WH101 were inoculated into GM17 medium with a 2% inoculation rate at pH 4.5 and were cultured at 30° C. for 48 hours. At the end of fermentation, the concentration of fermentation broth was determined. At pH 4.5, the $OD_{600}$ of mutant strain culture was 0.527, which increased by 5.5 times than that of the parent strain. The results are shown in Table 1.

TABLE 1

Growth performance of strains under acid stress

| Strain | *Lactococcus lactis* NZ9000 | *Lactococcus lactis* WH101 |
|---|---|---|
| $OD_{600}$ | 0.081 | 0.527 |

Example 3. Acid Tolerance Experiment

*Lactococcus lactis* NZ9000 and *Lactococcus lactis* WH101, which were preserved in −80° C. glycerol tube, were inoculated into GM17 medium at a 2% inoculation rate and incubated at 30° C. for 12 hours.

*Lactococcus lactis* NZ9000 and *Lactococcus lactis* WH101 were inoculated into GM17 medium at a 2% inoculation rate, respectively, and cultured at 30° C. until the logarithmic growth phase.

The cells were harvested by centrifugation at 5000 rpm for 10 min. Then they were washed twice with 0.85% normal saline and resuspended in GM17 (pH 4.0) medium, the suspension was kept for 1~3 h. The cells were washed twice with the same physiological saline and resuspended in an equal volume of physiological saline. 100 μl of the bacterial solution was applied to the plate after appropriate dilution and incubated at 30° C. for 24 hours to calculate the survival rate (Table 2). The survival rate of *Lactococcus lactis* WH101 was 4.1 times and 22.4 times than that of the parent strain after 2 hr and 3 hr under acid stress at pH 4.0, respectively.

TABLE 2

Acid tolerance experiment

| | Survival rate (%) | |
|---|---|---|
| Hours (h) | *Lactococcus lactis* NZ9000 | *Lactococcus lactis* WH101 |
| 0 | 100 | 100 |
| 1 | 65.08 | 74.34 |
| 2 | 0.99 | 4.04 |
| 3 | 0.05 | 1.11 |

Example 4. Other Environment Tolerance Experiments

The cells of the logarithmic growth phase were obtained according to Example 3. For ethanol tolerance experiment, the cells were washed twice with 0.85% normal saline and resuspended in GM17 (15% ethanol v/v) medium, and the suspension was kept for 1~3 hr. For oxygen tolerance experiment, the cells were resuspended and kept in GM17 (1 mmol/L $H_2O_2$) medium for different times. Lastly, for osmotic pressure tolerance experiment, the cells were resuspended in GM17 (15% NaCl v/v) medium for different times. The survival rates of the two strains were calculated in these environmental tolerance experiments (FIG. 1). The survival rate of the mutant strain was 5.2, 2.0 and 1.9 times over that of the parent strain treated with 15% ethanol for 4 hr, 15% NaCl for 6 hr and 1 mM $H_2O_2$ for 3 hr, respectively.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A mutant strain, named *Lactococcus lactis* WH101, with higher acid tolerance than that of its parent strain, which was deposited in the Chinese Type Culture Collection with the accession CCTCC NO: M 2016233.

2. The mutant strain of claim 1, wherein said mutant strain exhibits higher acid, ethanol, oxygen and osmotic pressure tolerance than that of its parent strain.

3. A method of for producing a fermentation food, comprising using the mutant strain of claim 1 as the fermentation strain to produce said fermentation food.

4. The method of claim 3 wherein said fermentation food is kimchi.

5. The method of claim 3 wherein said fermentation food is yoghurt.

* * * * *